(12) United States Patent
Nakamura (10) Patent No.: US 8,815,531 B2
(45) Date of Patent: Aug. 26, 2014

(54) DRY TEST STRIP AND METHOD FOR MEASURING CREATININE

(75) Inventor: Tsutomu Nakamura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 54 days.

(21) Appl. No.: 13/457,295

(22) Filed: Apr. 26, 2012

(65) Prior Publication Data

US 2012/0276568 A1    Nov. 1, 2012

(30) Foreign Application Priority Data

Apr. 28, 2011 (JP) ................................. 2011-102426

(51) Int. Cl.
*C12Q 1/34* (2006.01)
(52) U.S. Cl.
USPC .......................................................... 435/18
(58) Field of Classification Search
USPC .......................................................... 435/18
See application file for complete search history.

(56) References Cited

U.S. PATENT DOCUMENTS 6,479,249 B2 * 11/2002 Matsui et al. .................. 435/11

FOREIGN PATENT DOCUMENTS

| EP | 0281000 A2 | 9/1988 |
|---|---|---|
| JP | 02-283298 A | 11/1990 |
| JP | 04-311399 A | 11/1992 |
| JP | 09-061430 A | 3/1997 |
| JP | 4243255 B2 | 1/2009 |

OTHER PUBLICATIONS

Office Action issued Jun. 5, 2013 in corresponding Chinese Application No. 201210130423.06.
Extended European Search Report dated Dec. 20, 2013 in corresponding EP Application No. 12165787.8.

* cited by examiner

*Primary Examiner* — Chih-Min Kam
(74) *Attorney, Agent, or Firm* — Knobbe Martens Olson & Bear LLP (57) ABSTRACT

A dry test strip for measuring creatinine comprises: a support; a reagent layer that is disposed on the support; a reagent holding layer that is disposed on the reagent layer; and a connection layer that is composed of an adhesive which adhesively bonds the reagent layer to the reagent holding layer and is formed in spot form, wherein the reagent layer contains creatininase and 4-aminoantipyrine; the reagent holding layer contains creatinase, sarcosine oxidase, peroxidase, and N-ethyl-N-(2-hydroxy-3-sulfopropyl)-3,5-dimethoxyaniline; and the connection layer delays arrival of a liquid sample spot-deposited on the reagent holding layer at the reagent layer.

10 Claims, 4 Drawing Sheets

TIME (SEC) AFTER SPOT DEPOSITION OF SAMPLE

FIG. 2B

TIME (SEC) AFTER SPOT DEPOSITION OF SAMPLE

DRY TEST STRIP AND METHOD FOR MEASURING CREATININE

CROSS-REFERENCE TO RELATED APPLICATION

This application is based on Japanese Patent Application No. 2011-102426, filed on Apr. 28, 2011, the entire specification, claims, and drawings of which are incorporated by reference herein.

FIELD

The present invention relates to a dry test strip for measuring creatinine and a method for measuring creatinine.

BACKGROUND

Creatinine is an end product of a creatine pathway and has a structure in which creatine is dehydrated and cyclized. In the body, creatinine is present as creatine or creatine phosphate predominantly in the muscle. Creatine receives a high-energy phosphate from ATP to be transferred to creatine phosphate, which functions as an energy storage substance. Specifically, creatine phosphate provides a high-energy phosphate to ADP, and transfers to creatine or creatinine by a nonenzymatic reaction during energy consuming such as muscle contraction. Then, the generated creatinine is excreted into the urine through the kidney.

Therefore, an amount of creatinine excreted in the urine, i.e., a urinary concentration of creatinine is used as an indicator for muscle diseases or renal dysfunction. A blood creatinine level may also be an indicator for a disease such as renal dysfunction.

In the scene of group medical examination or in the situation of primary diagnosis such as screening examination, a dry test strip prepared by previously applying or impregnating a support with a reagent, which is colored by reacting with creatinine, and by drying the support has widely been used in order to quickly measure the urinary, serum, or plasma level of creatinine.

A dry test strip for measuring creatinine in accordance with the related art is prepared by utilizing a color reaction (Jaffe reaction) of a condensate of creatinine with picric acid under strong alkaline conditions. As one of such test strips, a test strip for measuring creatinine, which is composed of a support, a reagent layer containing 3,5-dinitrobenzoic acid carried on the support, and a development layer that is disposed on the reagent layer and contains a strong alkaline material such as lithium hydroxide is disclosed in Unexamined Japanese Patent Application KOKAI Publication No. H09-061430.

As the color reaction for measuring creatinine, an enzymatic method is also known. Japanese Patent No. 4243255 discloses a dry analysis element which quantifies gaseous ammonia generated by a reaction of creatinine with creatinine iminohydrase. Specifically, an indicator layer containing an indicator which produces a change detectable by gaseous ammonia, a liquid barrier layer through which the gaseous ammonia is passed, a reagent layer that contains an alkaline buffer and, as needed, can react with a matrix to generate ammonia, and a development layer are integrally layered on a transparent support in this order.

In addition, a creatinase-sarcosine oxidase-peroxidase method, which is one of enzymatic methods, has been utilized in wet creatinine measurement reagent kits in accordance with the related art. In "CRE-L Reagent Kainos Package Insert, Fourth Edition, Kainos Laboratories, Inc., 2010," "N-Assay CRE-L Nittobo Package Insert, Eleventh Edition, Nitto Boseki Co., Ltd., 2008," and "Exceliza CRE Package Insert, Sixth Edition, Sekisui Medical Co., Ltd., 2008," wet creatinine measurement reagent kits including first reaction reagents and second reaction reagents are disclosed. The first reaction reagent predecomposes endogenous creatine in a sample by creatininase. The second reaction reagent is added into the sample after a reaction by adding the first reaction reagent, creatinine in the sample is converted into creatine by creatininase, the creatine is decomposed into sarcosine and urea by creatinase, the sarcosine is reacted with sarcosine oxidase to produce hydrogen peroxide, and a quinone pigment is produced by oxidative condensation of a hydrogen donor compound and 4-aminoantipyrine in the presence of the hydrogen peroxide and peroxidase.

SUMMARY

However, the dry test strip for measuring creatinine using the Jaffe reaction in accordance with the related art, as disclosed in Unexamined Japanese Patent Application KOKAI Publication No. H09-061430, had the drawback of a large error in measurement of creatinine in a low-concentration range.

The dry analysis element as disclosed in Japanese Patent No. 4243255 had the drawbacks that the influence of endogenous ammonia in a sample was not able to be eliminated although an error in measurement of creatinine in a low-concentration range was smaller than that in the case of using the Jaffe reaction; and the element needed a complicated layer structure for controlling an ammonia gas as a reaction product and production yields were low.

In addition, since, in a dry test strip in accordance with the related art, all reagents contained in the test strip are taken in a sample and reacted, a reaction system including two or more stages cannot be applied to a dry test unless being via a gas such as an ammonia gas, as described in Japanese Patent No. 4243255. Therefore, the creatinase-sarcosine oxidase-peroxidase methods, as described in "CRE-L Reagent Kainos Package Insert, Fourth Edition, Kainos Laboratories, Inc., 2010," "N-Assay CRE-L Nittobo Package Insert, Eleventh Edition, Nitto Boseki Co., Ltd., 2008," and "Exceliza CRE Package Insert, Sixth Edition, Sekisui Medical Co., Ltd., 2008," which are two-stage reaction systems in which any gas is not generated in reaction processes, have not been able to be used for dry test strips until now.

The present invention has been accomplished with respect to the above-described problems and is aimed at providing a dry test strip for measuring creatinine, which produces a small error in measurement of creatinine in a low-concentration range and has a simple structure, and at providing a method for measuring creatinine using the test strip.

In order to achieve the above-described aims, a dry test strip for measuring creatinine in accordance with a first aspect of the present invention comprises:

a support;
a reagent layer that is disposed on the support;
a reagent holding layer that is disposed on the reagent layer; and
a connection layer that is disposed between the reagent layer and the reagent holding layer and connects the reagent layer to the reagent holding layer,
wherein
the reagent layer contains creatininase;
the reagent holding layer contains creatinase and sarcosine oxidase;

peroxidase, 4-aminoantipyrine, and a hydrogen donor compound are each contained only in any one layer or in both layers of the reagent layer and the reagent holding layer; and the connection layer delays arrival of a liquid sample spot-deposited on the reagent holding layer at the reagent layer.

The connection layer preferably comprises an adhesive applied to form a plurality of spots separated from each other, in which there is a part without the adhesive between the spots.

The hydrogen donor is preferably N-ethyl-N-(2-hydroxy-3-sulfopropyl)-3,5-dimethoxyaniline.

The reagent holding layer and/or the reagent layer preferably further comprise a buffer.

In order to achieve the above-described aims, a method for measuring creatinine in accordance with a second aspect of the present invention is a method for measuring creatinine using the dry test strip for measuring creatinine in accordance with the first aspect of the present invention, the method comprising:

a step of spot-depositing a liquid sample on the reagent holding layer;

a first measurement step of measuring a coloring degree of the dry test strip for measuring creatinine after finishing decomposition of endogenous creatine in the liquid sample by the creatinase;

a second measurement step of measuring a coloring degree of the dry test strip for measuring creatinine after a lapse of predetermined time from the first measurement step;

a step of subtracting the coloring degree measured in the first measurement step from the coloring degree measured in the second measurement step to acquire a variation between the coloring degrees in the first measurement step and the second measurement step; and a step of determining a creatinine level in the liquid sample by determining a value of a calibration curve corresponding to the variation.

In order to achieve the above-described aims, a method for measuring creatinine in accordance with a third aspect of the present invention is a method for measuring creatinine using the dry test strip for measuring creatinine in accordance with the first aspect of the present invention, the method comprising:

a spot deposition step of spot-depositing a liquid sample on the reagent holding layer;

a step of recording a coloring degree of the dry test strip for measuring creatinine over time after the spot deposition step until the dry test strip for measuring creatinine reacts with the liquid sample to make coloring reach a plateau;

a step of acquiring a variation per unit time of the coloring degree from an instant when a rate of change in the coloring degree is changed to an instant when the coloring reaches the plateau in the record; and a step of determining a creatinine level in the liquid sample by determining a value of a calibration curve corresponding to the variation.

BRIEF DESCRIPTION OF THE DRAWINGS

A more complete understanding of this application can be obtained when the following detailed description is considered in conjunction with the following drawings, in which.

DETAILED DESCRIPTION

Embodiments of the present invention will be described in detail below with reference to the drawings.

(Embodiments)

Figure 1A:
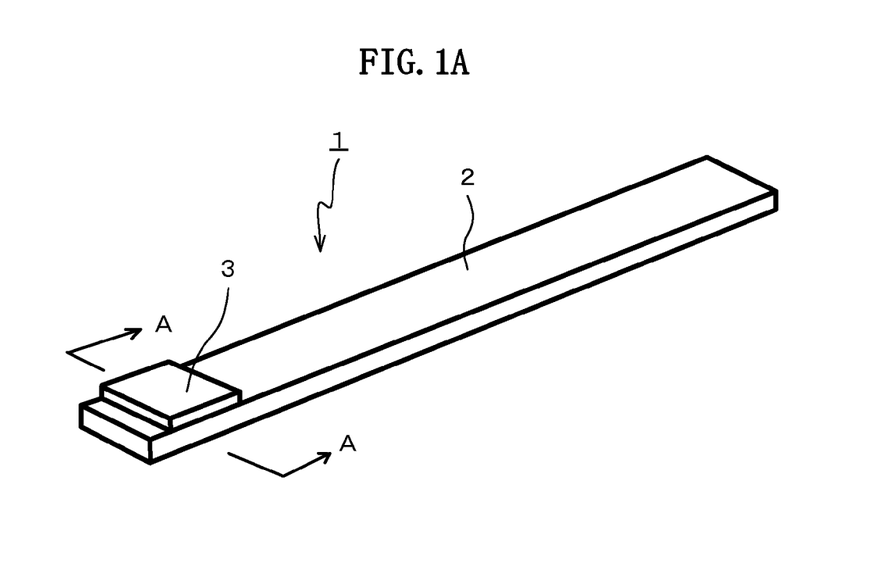
FIG. 1A is a perspective view illustrating the configuration of a dry test strip for measuring creatinine in accordance with an embodiment of the present invention.
Figure 1B:
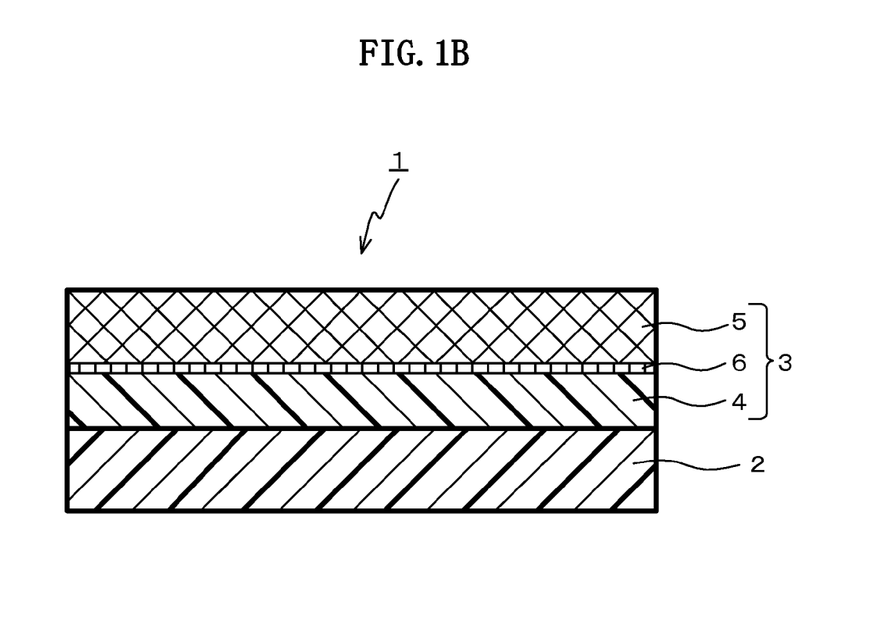
FIG. 1B is a longitudinal sectional view taken along the line A-A of FIG. 1A.
Figure 2A:
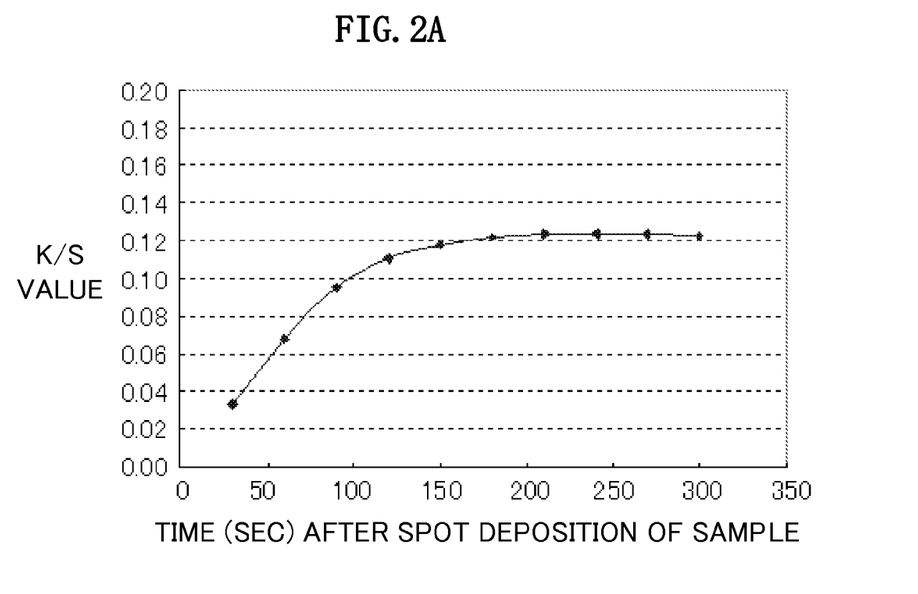
FIG. 2A is a diagram indicating a variation in K/S value over time when a high creatine sample is measured using a test strip for measuring creatinine in Example 1.

A dry test strip 1 for measuring creatinine in accordance with an embodiment of the present invention is composed of a support 2 and a reagent portion 3 that is carried on the support 2, as illustrated in FIG. 1A and FIG. 2A. The reagent portion 3 is composed of a reagent layer 4 that is formed on the support 2, a reagent holding layer 5 that is formed to cover the reagent layer 4, and a connection layer 6 that is formed between the reagent layer 4 and the reagent holding layer 5 and connects the reagent layer 4 to the reagent holding layer 5.

The support 2 preferably has no liquid permeability. As a result, when creatinine is measured using the dry test strip 1 for measuring creatinine in accordance with the present embodiment, the precise measurement can be made since a liquid sample spotted onto the reagent layer 4 and the reagent holding layer 5 remains in the reagent layer 4 and the reagent holding layer 5. As the support 2, a paper strip, a plastic (synthetic resin) piece, a metal piece, or the like may be used. The synthetic resin piece is preferably used from the viewpoints of mass productivity, a low cost, keeping quality, water resistance, and/or the like.

The support 2 preferably has optical transparency in the case of irradiation with light from a side closer to the support in optical analysis after having spotted a liquid sample to cause a detection reaction. In contrast, the optical transparency is not needed in the case of irradiation with light from a side closer to the reagent holding layer 5.

The reagent layer 4 contains creatininase. The reagent layer 4 is composed mainly of a material having liquid permeability. The reagent layer 4 is particularly preferably based on a water-soluble material, in which reagents are dispersed. As a result, the reagents contained in the reagent layer 4 are taken in the liquid sample spotted onto the reagent holding layer 5 located in an upper layer during the measurement. As the water-soluble material, water-soluble polymer compounds including polyvinylpyrrolidone (PVP) and/or the like may be used. The reagent layer 4 may also have the configuration in which the reagents are dispersed in a fabric material, such as paper, a knit, or a woven knit, having liquid permeability.

The reagent holding layer 5 contains creatinase and sarcosine oxidase. The reagent holding layer 5 is composed mainly of a material having liquid permeability. The reagent holding layer 5 is particularly preferably based on a water-soluble material, in which reagents are dispersed. As a result, the liquid sample spotted onto the reagent holding layer 5 is quickly and homogeneously diffused in the reagent holding layer 5 during the measurement. As the water-soluble material, water-soluble polymer compounds including polyvinylpyrrolidone (PVP) and/or the like may be used. The reagent holding layer 5 may also have the configuration in which the reagents are dispersed in a fabric material, such as paper, a knit, or a woven knit, having liquid permeability.

The connection layer 6 is formed by applying an adhesive to the surface of the reagent layer 4 so that a plurality of spots which are separated from each other are formed and by adhesively bonding the reagent layer 4 to the reagent holding layer 5. The connection layer 6 composed of the plurality of spot-shaped adhesives connects the reagent holding layer 5 to the reagent layer 4 so that slight gaps are sandwiched between the reagent holding layer 5 and the reagent layer 4. The presence of the gaps causes a delay in movement of a liquid sample from the reagent holding layer 5 to the reagent layer 4 when the sample is spot-deposited on the reagent holding layer 5. Therefore, the liquid sample spot-deposited on the reagent holding layer 5 is first preferentially diffused in the reagent holding layer 5 and then moved to the reagent layer 4.

In accordance with the present embodiment, a coloring reaction is performed by forming colored quinone by a coupling reaction of 4-aminoantipyrine with a hydrogen donor compound in the presence of hydrogen peroxide generated by hydrolysis of sarcosine by sarcosine oxidase and of peroxidase. Therefore, at least one layer of the reagent layer 4 and the reagent holding layer 5 contains peroxidase, 4-aminoantipyrine, and the hydrogen donor compound.

Such hydrogen donor compounds include N-(2-hydroxy-3-sulfopropyl)-3,5-dimethoxyaniline (HDAOS), N-ethyl-N-sulfopropyl-3-methoxyaniline (ADPS), N-ethyl-N-sulfopropylaniline (ALPS), N-ethyl-N-sulfopropyl-3,5-dimethoxyaniline (DAPS), N-sulfopropyl-3,5-dimethoxyaniline (HDAPS), N-ethyl-N-sulfopropyl-3,5-dimethylaniline (MAPS), N-ethyl-N-sulfopropyl-3-methylaniline (TOPS), N-ethyl-N-(2-hydroxy-3-sulfopropyl)-3-methoxyaniline (ADOS), N-ethyl-N-(2-hydroxy-3-sulfopropyl)aniline (ALOS), N-ethyl-N-(2-hydroxy-3-sulfopropyl)-3,5-dimethoxyaniline (DAOS), N-ethyl-N-(2-hydroxy-3-sulfopropyl)-3,5-dimethylaniline (MAOS), N-ethyl-N-(2-hydroxy-3-sulfopropyl)-3-methylaniline (TOOS), N-sulfopropylaniline (HALPS), and the like.

The reagent layer 4 and/or the reagent holding layer 5 may contain a buffer for enhancing the stability of the reaction or preservation of enzymes contained in the reagent layer 4 and the reagent holding layer 5. A potential Hydrogen (pH) is preferably in the range of pH 6-9. As the buffer, a known buffer such as a phosphate buffer, N,N-bis(2-hydroxyethyl)-2-aminomethanesulfonic acid (BES), N-tris(hydroxymethyl)methyl-2-aminomethanesulfonic acid (TES), 2-[4-(2-hydroxyethyl)-1-piperazyl]ethanesulfonic acid (HEPES), or piperazine-1,4-bis(2-hydroxy-3-propanesulfonic acid), dihydrate (POPSO) may be used.

When a liquid sample intended to be measured by the dry test strip 1 for measuring creatinine has a very small amount of, e.g., around 5 µl, the reagent layer 4 and the reagent holding layer 5 may have an area of around several millimeters×several millimeters. Furthermore, since it is difficult to hold these layers by a hand and/or the like, the support 2 is preferably disposed as a long and narrow piece with a width of around several millimeters×1 cm to be able to be used as a handle.

In addition, for the content of each reagent in the dry test strip 1 for measuring creatinine, the content of creatininase may be at least enough to react with the predetermined measuring upper limit of creatinine. The contents of the other reagents may be at least enough to react with endogenous creatine in the liquid sample as well as the predetermined measuring upper limit of creatinine.

For example, when serum is measured, the levels of creatinine and creatine in the serum including one originated from a patient are about 0.3-20 mg/dl and about 0.2-0.6 mg/dl, respectively. NCCLS (National Committee for Clinical Laboratory Standards) specifies that, when an object substance is measured, an interfering substance having an influence on the measurement may be based on around three times the upper limit of the interfering substance. Thus, the level of each reagent may be determined based on the measuring upper limit of creatinine of 20 mg/dl and the reference value of an endogenous creatine level of 1.8 mg/dl. A blood creatine level may also be increased in a healthy subject by taking a supplement and/or the like. Therefore, it is further preferable to determine the reference value of an endogenous creatine level in contemplation of such an anticipated increase in blood creatine level. For example, in the case of the above-described example, it is further preferable to set the reference value of an endogenous creatine level at 5.0 mg/dl.

The preferred concentration of each reagent in a reaction liquid formed when the liquid sample is spotted is as follows:

Creatininase: 20-1,000 U/ml
Creatinase: 20-1,000 U/ml
Sarcosine oxidase: 20-300 U/ml
Peroxidase: 50-3,000 U/ml
4-Aminoantipyrine: 5-100 mM
Hydrogen donor compound: 5-100 mM The dry test strip 1 for measuring creatinine in accordance with an embodiment of the present invention can be produced as described below.

First, a sheet having a predetermined material and a predetermined thickness to be the support 2 is cut as a long and narrow piece with predetermined dimensions. The support 2 is produced by cleaning and drying the long and narrow piece.

Then, the reagent layer 4 is produced. First, as needed, peroxidase, 4-aminoantipyrine, a hydrogen donor compound, and a buffer for pH as well as creatininase are dispersed in a material having liquid permeability.

When the material having liquid permeability is a water-soluble material such as a water-soluble polymer compound, the material is dissolved in pure water to make an aqueous solution and is dispersed by dissolving the above-described respective reagents in the aqueous solution and stirring the resultant. The resultant is applied to the predetermined part of the support 2 and dried to make the reagent layer 4.

When the material having liquid permeability is a fabric material such as paper, a knit, or a woven knit, an aqueous solution prepared by dissolving the above-described respective reagents in pure water and stirring the resultant is dispersed by making the fabric material with the predetermined dimensions absorb the aqueous solution. The material is dried to remove water and to make the reagent layer 4. Then, the reagent layer 4 is layered on the support 2. As a method therefor, when the reagent layer 4 is based on a water-soluble material, the bottom face of the reagent layer 4 is wet with pure water and is fit to the predetermined position of the support 2 by pressure. Thereby, the water-soluble material on the bottom face is dissolved and functions as an adhesive. Alternatively, the reagent layer 4 may also be adhesively bonded onto the support 2 with an adhesive.

Then, the reagent holding layer 5 is produced. First, for the reagent holding layer 5, as needed, peroxidase, 4-aminoantipyrine, a hydrogen donor compound, and a buffer for pH as well as creatinase and sarcosine oxidase are dispersed in a material having liquid permeability.

When the material having liquid permeability is a water-soluble material such as a water-soluble polymer compound, the material is dissolved in pure water to make an aqueous solution and is dispersed by dissolving the above-described respective reagents in the aqueous solution and stirring the resultant. The resultant is applied to a flat substrate, dried, and pulled off the substrate to make the reagent holding layer 5.

When the material having liquid permeability is a fabric material such as paper, a knit, or a woven knit, an aqueous solution prepared by dissolving the above-described respective reagents in pure water and stirring the resultant is dispersed by making the fabric material with the predetermined dimensions absorb the aqueous solution. The material is dried to remove water and to make the reagent holding layer 5.

Then, the reagent holding layer 5 is layered on the reagent layer 4 and adhesively bonded using an adhesive. The adhesive may be one that dose not inhibit the reactions of the above-described respective enzymes. It is preferable to apply the adhesive so that a plurality of spots separated from each other are formed on the reagent layer and to adhesively bond the reagent holding layer 5 so that a part without the adhesive is formed between the spots. As a result, the connection layer 6 is formed.

In such a manner, the dry test strip 1 for measuring creatinine in accordance with an embodiment of the present invention may be produced.

A method for measuring a creatinine level from a liquid sample such as serum, plasma, or urine using the test strip according to the present embodiment will be described below.

First, a liquid sample is spot-deposited to the reagent holding layer 5. The spot-deposited liquid sample takes in the various reagents contained in the reagent holding layer 5 while being diffused laterally in the reagent holding layer 5. When this occurs, endogenous creatine contained in the sample is first decomposed into urea and sarcosine by the function of taken creatinase. Then, hydrogen peroxide is generated by the hydrolysis of the sarcosine by the function of sarcosine oxidase taken in the sample.

[Formula 1]

In parallel with the proceeding of the above-described reaction, the sample diffused in the reagent holding layer 5 then arrives at the reagent layer 4. The diffusion of the sample gradually proceeds as described above because the reagent holding layer 5 and the reagent layer 4 are connected via slight gaps by the connection layer 6. The sample arrives at the reagent layer 4 after an enzyme reaction by creatinase and sarcosine oxidase proceeds to some extent in the reagent holding layer 5 in the test strip according to the present embodiment by the gradual proceeding of the diffusion of the sample. Then, the sample finally takes in creatininase in the reagent layer 4 and creatinine in the sample is converted into creatine by the function of the creatininase. Then, hydrogen peroxide is generated depending on the amount of the creatine originated from the creatinine by the functions of the creatinase and the sarcosine oxidase that have already been taken in the sample. Since the reagent holding layer 5 and the reagent layer 4 contain peroxidase, 4-aminoantipyrine, and the hydrogen donor compounds, a quinone pigment of which the amount depends on the amount of hydrogen peroxide is formed in the sample in this stage by the coloring reaction by these reagents.

[Formula 2]

As described above, the quinone pigment is formed depending on the amount of generated hydrogen peroxide originated from endogenous creatine and the amount of the generated hydrogen peroxide originated from the creatine originated from the creatinine. Since the generation of the hydrogen peroxide originated from the endogenous creatine is started prior to the generation of the hydrogen peroxide originated from the creatine originated from the creatinine, the generation of the hydrogen peroxide originated from the creatine originated from the creatinine can continue even after the endogenous creatine has been consumed to finish the generation of the hydrogen peroxide originated from endogenous creatine. The endogenous creatine can be distinguished from the creatine originated from the creatinine by a time lag between the reactions of the endogenous creatine and the creatine originated from the creatinine.

Specifically, a coloring degree (K/S value) is measured over time using an optical measurer after the spot deposition of the sample. A measurement wavelength may be a wavelength close to the absorption peak of the formed colored quinone and is preferably 400-700 nm, particularly preferably 580-640 nm. After a coloring reaction has reached a plateau, a variation in K/S value over time is analyzed. In this case, it can be estimated that the generation of the hydrogen peroxide originated from the endogenous creatine is finished and the state of the continuing generation of the hydrogen peroxide originated from the creatine originated from the creatinine is started at the point where the inclination of the K/S values plotted over time is changed. This is because the rate of the generation of hydrogen peroxide originated from endogenous creatine is different from the rate of the generation of hydrogen peroxide originated from creatine originated from creatinine since the rates of the reactions of creatinase and creatininase with respective matrices are different. The amount of coloring originated from the creatinine contained in the sample can be determined while eliminating the influence of the endogenous creatine by reading a variation per unit time in the K/S value in the time range where only the generation of the hydrogen peroxide originated from the creatine originated from the creatinine continues. Finally, the level of the creatinine contained in the sample is determined, e.g., by comparing the detected variation per unit time in the K/S value to the previously made calibration curve.

The variation per unit time in the K/S value in the time range where only the generation of the hydrogen peroxide originated from the creatine originated from the creatinine continues can also be determined by performing the first measurement of a K/S value after a lapse of predetermined time t1 after spot deposition of the did liquid sample, then performing the second measurement of a K/S value after a further lapse of predetermined time t2, and determining a difference between the second measured K/S value and the first measured K/S value, instead of the measurement of the K/S values over time. The predetermined time t1 may be not less than the upper limit of time until the generation of the hydrogen peroxide originated from the endogenous creatine is finished when the present test strip is reacted with the sample. The amount of endogenous creatine contained in a liquid sample such as serum, plasma, or urine is generally within a certain range every time the liquid sample is originated. Therefore, the upper limit of the time until the generation of the hydrogen peroxide originated from the endogenous creatine is finished when the present test strip is reacted with the sample can be estimated from the origin and measurement amount of the liquid sample. The predetermined time t2 may be less than time until the generation of hydrogen peroxide is finished when the present test strip is reacted with a liquid sample containing creatinine with the measurement lower limit. When a liquid sample containing creatinine within an intended measurement range is measured with the present test strip, the predetermined time t2 is made to be in a time period in which a coloring reaction continues by setting the predetermined time t2 in such a manner. When the predetermined time t2 is out of the time period in which the coloring reaction continues, the linearity of the calibration curve may be lost and a creatinine level may not be measured accurately.

(Variation Embodiments)

In the above embodiment, the connection layer 6 is formed with the plurality of spot-shaped adhesives, but, instead, the connection layer 6 may also be formed by adhesively bonding the reagent layer 4 to the reagent holding layer 5 with an adhesive with liquid permeability applied to the whole face of the reagent layer 4. In this case, the adhesive, in which the infiltration rate of the liquid sample is lower than the diffusion rate of the liquid sample in the reagent holding layer 5, is preferably used. When the connection layer 6 is composed of such an adhesive, the liquid sample spot-deposited to the reagent holding layer 5 is diffused more preferentially in the reagent holding layer 5 than in the connection layer 6. Therefore, the liquid sample is diffused in the reagent holding layer 5 to some extent and then arrives at the reagent layer 4 with the time lag of infiltrating the connection layer 6. That is, the transfer of the sample from the reagent holding layer 5 to the reagent layer 4 is delayed for the time of infiltrating the connection layer 6.

In addition to Variation Embodiment as described above, the connection layer 6 has such an optional structure that the time of transferring the liquid sample from the reagent holding layer 5 to the reagent layer 4 is longer than transfer time in the case of adhesion between the reagent holding layer 5 and the reagent layer 4 without the connection layer 6. For example, in accordance with the embodiment, the connection layer 6 composed of the plurality of spot-shaped adhesives is used to dispose the gaps between the reagent holding layer 5 and the reagent layer 4 but, instead, a connection layer 6 composed of a mesh-like cloth with liquid permeability impregnated with an adhesive may also be used. One surface of the reagent holding layer 5 facing the reagent layer 4 may also be impregnated with a water-insoluble polymer that deteriorates liquid permeability to make a connection layer 6. When the connection layer 6 is produced, the connection between the reagent holding layer 5 and the reagent layer 4 may be performed by fitting the connection layer 6 in a wet state to the reagent layer 4 by pressure without using any adhesive and thereafter drying the connection layer 6. When the bottom face of the reagent holding layer 5 is wet with pure water and the reagent holding layer 5 is layered on the reagent layer 4 and dried to adhesively bond the reagent holding layer 5 to the reagent layer 4, the bottom face of the reagent holding layer 5 may also function as a connection layer 6.

EXAMPLE 1

The present invention is described in more detail below with reference to Examples but is not limited to the scope of Examples below. Unless otherwise specified, deionized water was used as pure water.

First, a long and narrow piece having dimensions of 70 mm in length×5 mm in width was cut as a support from a white polyethylene terephthalate (PET) sheet with a thickness of 0.2 mm.

Then, 300 U of creatininase (manufactured by Kikkoman Corporation), 81 mg of 4-aminoantipyrine (manufactured by Kishida Chemical Co., Ltd.), and 435 mg of sodium alginate (manufactured by Nacalai Tesque, Inc.) were dissolved in 22 ml of phosphate buffer (pH 7.5). The aqueous solution was thoroughly stirred and was thereafter degassed. The total amount of the solution was applied to one end of the support to have dimensions of 7 mm in length×5 mm in width×0.1 mm in thickness. Then, the solution was dried at 40° C. for 20 minutes to completely evaporate water and a film-shaped reagent layer was made.

A reagent holding layer composed mainly of a fabric material was layered on the reagent layer. Savina® from KB Seiren, Ltd. was used as the fabric material. In 12 mL of phosphate buffer (pH 7.5), 49 mg of N-ethyl-N-(2-hydroxy-3-sulfopropyl)-3,5-dimethylaniline sodium salt (DAOS) (manufactured by Dojindo Laboratories Co., Ltd.), 10 KU of creatinase (manufactured by Kikkoman Corporation), 600 U of sarcosine oxidase (manufactured by Kikkoman Corporation), and 10 KU of peroxidase (manufactured by Toyobo Co., Ltd.) were dissolved. The aqueous solution was thoroughly stirred and was thereafter degassed. Savina of 7 mm in length×5 mm in width×0.2 mm in thickness was impregnated with the total amount of the solution. Then, the solution was dried at 40° C. for 20 minutes to evaporate water.

This reagent holding layer was adhesively bonded and layered onto the reagent layer using an adhesive. An acrylic adhesive was used as the adhesive and applied onto the reagent layer in dot form and the adhesive bonding was performed so that a part without the adhesive was formed between the dots.

EXAMPLE 2

A support, a reagent layer, and a reagent holding layer were produced in a similar manner to that of Example 1. However, instead of adhesively bonding the reagent holding layer onto the reagent layer using the adhesive, the bottom face of the reagent holding layer was wet with pure water and the reagent holding layer was layered on the reagent layer and dried to adhesively bond the layers.

(Time Course of Reaction of Creatine with Creatinine)

Figure 2B:
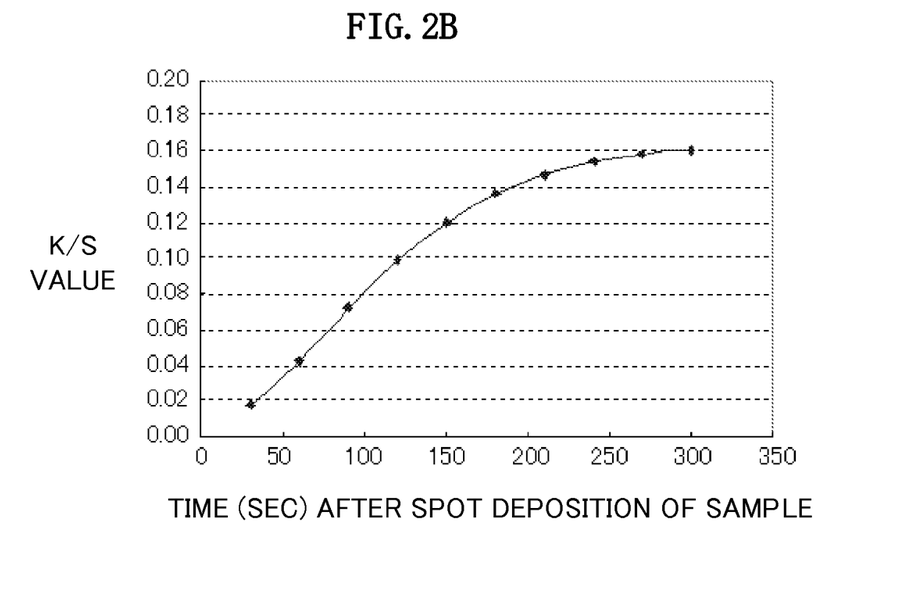
FIG. 2B is a diagram indicating a variation in K/S value over time when a high creatinine sample is measured.

To examine whether or not a coloring reaction with endogenous creatine can be distinguished from a coloring reaction with creatine originated from creatinine, variations in coloring degree (K/S value) with time were compared when a sample A with a large amount of creatine (creatinine level of 0.79 mg/dL and creatine level of 5.47 mg/dL) and a sample B with a large amount of creatinine (creatinine level of 5.08 mg/dL and creatine level of 0.49 mg/dL) were reacted with such test strips for measuring creatinine in accordance with Example 1. A tabletop reflectometer, Spotchem® EZ, from Arkray, Inc. was used as a measuring apparatus. The test strips were placed on the table and 5.0 µl of samples were spot-deposited from above. Then, reflectivities (R) at a wavelength of 610 nm were measured over time. The reflectivities (R) were converted into K/S values according to the Kubelka-Munk equation $(K/S=(1-R)^2/2R)$. The six measurements were performed for each sample. It is FIG. 2A which indicates the variation in the coloring reaction of the sample A with time and it is FIG. 2B which indicates the variation in the coloring reaction of the sample B with time. In the respective diagrams, mean values in the six measurements are plotted as the K/S values of the samples A and B. As can be seen from FIG. 2A, the coloring reaction from the endogenous creatine arrives at the plateau 180 seconds after the spot deposition of the sample. In contrast, as can be seen from FIG. 2B, the coloring reaction with the creatine originated from the creatinine in the sample continues up to 300 seconds after the spot deposition of the sample. Thus, it was found that the amount of a color reaction with creatine originated from creatinine, namely, the amount of the creatine in a sample can be determined by calculating a variation in absorbance for 180-300 seconds after spot deposition of the sample.

(Measurement Operation)

In the present example, based on the findings as described above, creatinine levels were measured using test strips for measuring creatinine as described below. The tabletop reflectometer, Spotchem® EZ, from Arkray, Inc. was used as a measuring apparatus. The test strips for measuring creatinine were placed on the table and 5.0 µl of samples were spot-deposited from above. Then, reflectivities (R) at a wavelength of 610 nm were measured over time. The reflectivities (R) were converted into K/S values according to the Kubelka-Munk equation $(K/S=(1-R)^2/2R)$. By measuring a sample with a known level, the calibration curve of a variation in K/S value (ΔK/S value) between 180 seconds and 300 seconds after the measurement and a creatinine level was previously made. The creatinine levels in the samples were calculated based on the variation in K/S value between 180 seconds and 300 seconds after the measurement and the calibration curve. Hereinafter, this method for measuring a K/S value is referred to as a reaction time lag measuring method.

(Influence of Endogenous Creatine Level)

To investigate the presence or absence of the influence of endogenous creatine in the test strips for measuring creatinine in accordance with Example 1, the creatine levels of a sample C (creatine level of 0.42 mg/dL) and a sample D (creatine level of 5.59 mg/dL) which had the same creatinine level (0.54 mg/dL) but had different creatine levels were measured six times with the test strips for measuring creatinine in accordance with Example 1. As a result, the mean creatine levels of the sample C and the sample D, measured with the test strips for measuring creatinine in accordance with Example 1, were 0.52 mg/dL and 0.52 mg/dL, respectively. When the creatine levels were measured with the test strips for measuring creatinine in accordance with Example 1 in combination with the reaction time lag measuring method, no influence of endogenous creatine was observed.

(Correlation Test)

Figure 3:
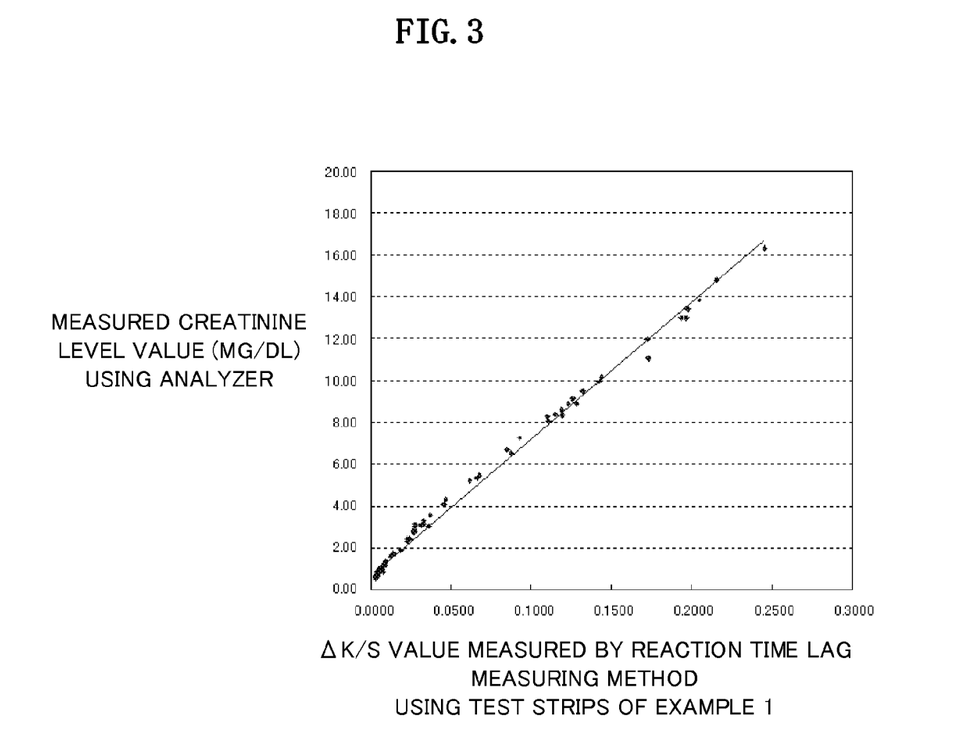
FIG. 3 is a diagram indicated by plotting ΔK/S values measured by a reaction time lag measurement method using the dry test strip for measuring creatinine in Example 1 and measured creatinine levels measured using an analyzer.

To compare the accuracies of the test strips for measuring creatinine in accordance with Example 1, creatinine levels in serum samples from 85 subjects, of which the creatinine levels had previously been measured, were measured by a creatinine analyzer (manufactured by Eiken Chemical Co., Ltd.). It is FIG. 3 which is prepared by plotting the measured creatinine level values (0.54-16.33 mg/dL) measured using the analyzer and the ΔK/S values measured by the reaction time lag measuring method using the test strips for measuring creatinine in accordance with Example 1. The measured values in the case of using the analyzer and the ΔK/S values measured by the reaction time lag measuring method using the test strips for measuring creatinine in accordance with Example 1 exhibited a strong correlation of 0.99. In addition, as a result of this test, it was found that measurement results with good linearity were obtained in the wide level range of 0.54-16.33 mg/dL in the measurement of the creatinine levels with the test strips for measuring creatinine in accordance with Example 1.

(Simultaneous Measurement Test)

To examine the within-run reproducibilities and accuracies of the test strips for measuring creatinine in accordance with Example 1, the creatinine levels of two samples having different creatinine levels, a sample E (creatinine level of 0.75 mg/dL) and a sample F (creatinine level of 9.14 mg/dL) were simultaneously measured 24 times, respectively. As a result, the mean creatine levels of the sample E and the sample F, measured with the test strips for measuring creatinine in accordance with Example 1, were 0.78 mg/dL and 9.17 mg/dL, respectively. In addition, the coefficients of variation of the respective sample measured with the test strips for measuring creatinine in accordance with Example 1 were 3% or less, which exhibited very good within-run reproducibilities.

TABLE 1

|  | sample E | sample F |
| --- | --- | --- |
| Assayed value (md/dL) | 0.79 | 9.14 |
| 1 | 0.77 | 9.07 |
| 2 | 0.79 | 9.31 |
| 3 | 0.78 | 8.67 |
| 4 | 0.78 | 9.15 |
| 5 | 0.78 | 9.22 |
| 6 | 0.76 | 9.36 |
| 7 | 0.73 | 8.70 |
| 8 | 0.79 | 9.29 |
| 9 | 0.77 | 8.96 |
| 10 | 0.79 | 9.21 |
| 11 | 0.78 | 9.18 |
| 12 | 0.79 | 9.58 |
| 13 | 0.76 | 9.12 |
| 14 | 0.78 | 9.37 |
| 15 | 0.78 | 9.42 |
| 16 | 0.80 | 9.47 |
| 17 | 0.75 | 8.97 |
| 18 | 0.83 | 9.10 |
| 19 | 0.79 | 8.98 |
| 20 | 0.77 | 9.32 |
| 21 | 0.74 | 8.97 |
| 22 | 0.78 | 9.50 |
| 23 | 0.74 | 8.99 |
| 24 | 0.80 | 9.18 |
| Mean value (mg/dL) | 0.78 | 9.17 |
| Standard deviation | 0.022 | 0.233 |
| Coefficient of variation | 2.8 | 2.5 |

(Comparison of Influences of Connection Layers)

Figure 4A:
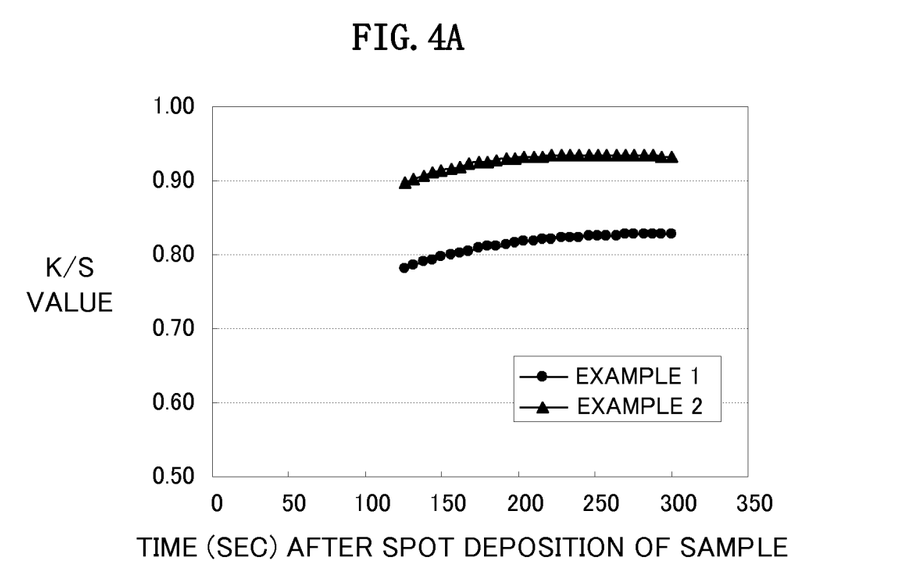
FIG. 4A is a diagram indicating variations in K/S values over time when the values are measured for samples with low creatinine levels using test strips for measuring creatinine in Examples 1 and 2.
Figure 4B:
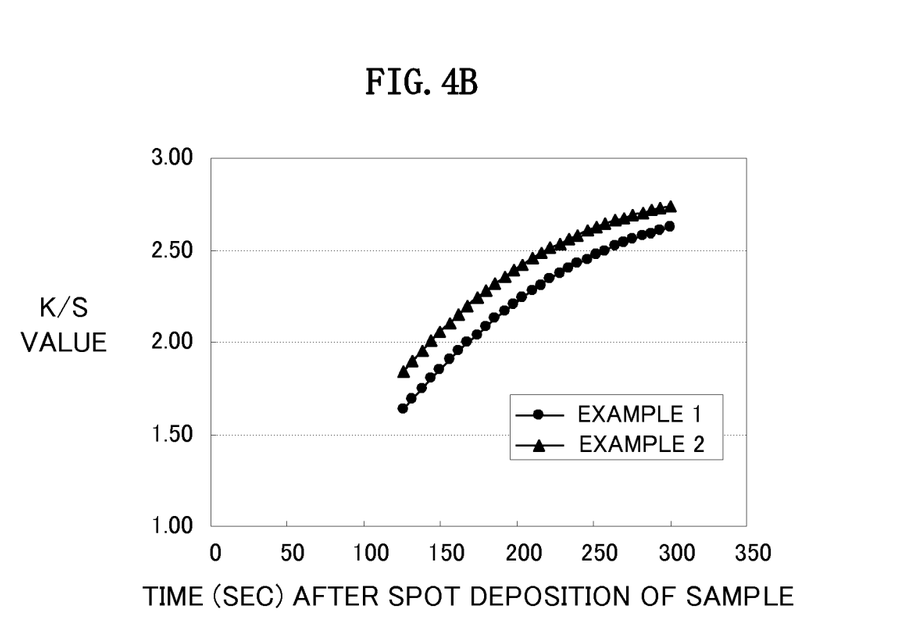
FIG. 4B is a diagram indicating variations in K/S values over time when the values are measured for samples with high creatinine levels.

To examine the influences of the properties of connection layers on the reaction time lag measuring method, the K/S values of a sample G (creatinine level of 0.89 mg/dL and creatine level of 6.1 mg/dl) and a sample H (creatinine level of 22.30 mg/dL and creatine level of 5.8 mg/dl) were measured over time using the test strips for measuring creatinine in accordance with Example 1 and Example 2 having the different connection layers. FIG. 4A indicates variations in K/S values over time when the values were measured for samples with low creatinine levels; and FIG. 4B indicates variations in K/S values over time when the values were measured for samples with high creatinine levels. In addition, the creatinine level values measured with the respective test strips for measuring creatinine are listed in Table 2. As is apparent from the reaction time courses indicated in FIG. 4A and FIG. 4B, for both samples, the test strips for measuring creatinine in accordance with Example 2 indicated higher K/S values than those indicated by the test strips for measuring creatinine in accordance with Example 1. This is considered to be because the samples were immediately moved from the reagent holding layer to the reagent layer in the test strips for measuring creatinine in accordance with Example 2 compared to the test strips for measuring creatinine in accordance with Example 1, therefore time where endogenous creatine was reacted without coloring in the reagent holding layer was short, and consequently a larger amount of hydrogen peroxide originated from the endogenous creatine caused a coloring reaction. In addition, as listed in Table 2, the measurement results in the case of using the test strips for measuring creatinine in accordance with Example 2 indicated lower values than those in the case of using the test strips for measuring creatinine in accordance with Example 1. This is considered to be because the samples were immediately moved from the reagent holding layer to the reagent layer in the test strips for measuring creatinine in accordance with Example 2 compared to the test strips for measuring creatinine in accordance with Example 1, therefore the movement occurred at an earlier time point than that at which the coloring reaction of creatinine occurred, and consequently most of the creatinine in the samples had already been consumed in the measurement time period of 180-300 seconds. Furthermore, in comparison between the samples G and H with the different creatinine levels, the divergences between the actual creatinine levels and the measured values were similar in both samples when the test strips for measuring creatinine in accordance with Example 1 were used. In contrast, the divergence between the actual creatinine level and the measured value in the sample H with the high creatinine level was greater than that in the sample G when the test strips for measuring creatinine in accordance with Example 2 were used. From this, the measurement of creatinine with a high level is considered to be susceptible to the influence of endogenous creatine when a sample is immediately moved from the reagent holding layer to the reagent layer as in the case of the test strips for measuring creatinine in accordance with Example 2.

TABLE 2

| | Example 1 | | Example 2 | |
| --- | --- | --- | --- | --- |
| Sample | Measured value(mg/dL) | Divergence (%) | Measured value(mg/dL) | Divergence (%) |
| G | 0.98 | 9.65 | 0.78 | −12.46 |
| H | 19.68 | −11.77 | 17.72 | −20.54 |

Having described and illustrated the principles of this application by reference to one or more preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. A dry test strip for measuring creatinine comprising:
    a support;
    a reagent layer that is disposed on the support;
    a reagent holding layer that is disposed on the reagent layer; and
    a connection layer that is disposed between the reagent layer and the reagent holding layer and connects the reagent layer to the reagent holding layer,
    wherein
    the reagent layer contains creatininase;
    the reagent holding layer contains creatinase and sarcosine oxidase;
    peroxidase, 4-aminoantipyrine, and a hydrogen donor compound are each contained only in any one layer or in both layers of the reagent layer and the reagent holding layer; and
    the connection layer comprises an adhesive applied to form a plurality of spots separated from each other, so as to comprise a part without the adhesive between the reagent holding layer and the reagent layer, which causes a delay in a movement of a liquid sample therebetween, when the sample is spot-deposited on the reagent holding layer.

2. The dry test strip for measuring creatinine according to claim 1, wherein the hydrogen donor is N-ethyl-N-(2-hydroxy-3-sulfopropyl)-3,5-dimethoxyaniline.

3. The dry test strip for measuring creatinine according to claim 2, wherein the reagent holding layer and/or the reagent layer further comprise a buffer.

4. A method for measuring creatinine using the dry test strip for measuring creatinine according to claim 2, the method comprising:
    a step of spot-depositing a liquid sample on the reagent holding layer;
    a first measurement step of measuring a coloring degree of the dry test strip for measuring creatinine after finishing decomposition of endogenous creatine in the liquid sample by the creatinase;
    a second measurement step of measuring a coloring degree of the dry test strip for measuring creatinine after a lapse of predetermined time from the first measurement step;
    a step of subtracting the coloring degree measured in the first measurement step from the coloring degree measured in the second measurement step to acquire a variation between the coloring degrees in the first measurement step and the second measurement step; and
    a step of determining a creatinine level in the liquid sample by determining a value of a calibration curve corresponding to the variation.

5. A method for measuring creatinine using the dry test strip for measuring creatinine according to claim 2, the method comprising:
    a spot deposition step of spot-depositing a liquid sample on the reagent holding layer;
    a step of recording a coloring degree of the dry test strip for measuring creatinine over time after the spot deposition step until the reaction of the dry test strip with the liquid sample making the coloring degree reach a plateau,
    a step of acquiring a variation per unit time of the coloring degree from an instant when a rate of change in the coloring degree is changed to an instant when the coloring degree reaches the plateau in the record; and a step of determining a creatinine level in the liquid sample by determining a value of a calibration curve corresponding to the variation.

6. The dry test strip for measuring creatinine according to claim 1, wherein the reagent holding layer and/or the reagent layer further comprise a buffer.

7. A method for measuring creatinine using the dry test strip for measuring creatinine according to claim 6, the method comprising:
- a step of spot-depositing a liquid sample on the reagent holding layer;
- a first measurement step of measuring a coloring degree of the dry test strip for measuring creatinine after finishing decomposition of endogenous creatine in the liquid sample by the creatinase;
- a second measurement step of measuring a coloring degree of the dry test strip for measuring creatinine after a lapse of predetermined time from the first measurement step;
- a step of subtracting the coloring degree measured in the first measurement step from the coloring degree measured in the second measurement step to acquire a variation between the coloring degrees in the first measurement step and the second measurement step; and
- a step of determining a creatinine level in the liquid sample by determining a value of a calibration curve corresponding to the variation.

8. A method for measuring creatinine using the dry test strip for measuring creatinine according to claim 6, the method comprising:
- a spot deposition step of spot-depositing a liquid sample on the reagent holding layer; a step of recording a coloring degree of the dry test strip for measuring creatinine over time after the spot deposition step until the reaction of the dry test strip with the liquid sample making the coloring reach a plateau;
- a step of acquiring a variation per unit time of the coloring degree from an instant when a rate of change in the coloring degree is changed to an instant when the coloring degree reaches the plateau in the record; and
- a step of determining a creatinine level in the liquid sample by determining a value of a calibration curve corresponding to the variation.

9. A method for measuring creatinine using the dry test strip for measuring creatinine according to claim 1, the method comprising:
- a step of spot-depositing a liquid sample on the reagent holding layer;
- a first measurement step of measuring a coloring degree of the dry test strip for measuring creatinine after finishing decomposition of endogenous creatine in the liquid sample by the creatinase;
- a second measurement step of measuring a coloring degree of the dry test strip for measuring creatinine after a lapse of predetermined time from the first measurement step;
- a step of subtracting the coloring degree measured in the first measurement step from the coloring degree measured in the second measurement step to acquire a variation between the coloring degrees in the first measurement step and the second measurement step; and
- a step of determining a creatinine level in the liquid sample by determining a value of a calibration curve corresponding to the variation.

10. A method for measuring creatinine using the dry test strip for measuring creatinine according to claim 1, the method comprising:
- a spot deposition step of spot-depositing a liquid sample on the reagent holding layer;
- a step of recording a coloring degree of the dry test strip for measuring creatinine over time after the spot deposition step until the reaction of the dry test strip with the liquid sample making the coloring degree reach a plateau;
- a step of acquiring a variation per unit time of the coloring degree from an instant when a rate of change in the coloring degree is changed to an instant when the coloring degree reaches the plateau in the record; and
- a step of determining a creatinine level in the liquid sample by determining a value of a calibration curve corresponding to the variation.

* * * * *